United States Patent
Andreucci et al.

(10) Patent No.: US 9,016,125 B2
(45) Date of Patent: Apr. 28, 2015

(54) NEMS COMPRISING ALSI ALLOY BASED TRANSDUCER

(75) Inventors: Philippe Andreucci, Moirans (FR); Laurent Duraffourg, Voiron (FR); Carine Marcoux, Voiron (FR); Pierre Brianceau, Biviers (FR); Sebastien Hentz, Varces (FR); Stephane Minoret, Grenoble (FR); Edward Myers, Sherman Oaks, CA (US); Michael Roukes, Pasadena, CA (US)

(73) Assignees: Commissariat à l'énergie et aux énergies alternatives, Paris (FR); California Institute of Technology, Pasadena, CA (US)

( * ) Notice: Subject to any disclaimer, the term of this patent is extended or adjusted under 35 U.S.C. 154(b) by 673 days.

(21) Appl. No.: 13/384,474

(22) PCT Filed: Jul. 13, 2010

(86) PCT No.: PCT/EP2010/060033
§ 371 (c)(1),
(2), (4) Date: Jul. 18, 2012

(87) PCT Pub. No.: WO2011/006885
PCT Pub. Date: Jan. 20, 2011

(65) Prior Publication Data
US 2012/0272742 A1   Nov. 1, 2012

Related U.S. Application Data

(60) Provisional application No. 61/226,419, filed on Jul. 17, 2009.

(30) Foreign Application Priority Data

Jul. 17, 2009 (FR) ...................................... 09 54998

(51) Int. Cl.
G01P 15/10 (2006.01)
G01P 15/097 (2006.01)
(Continued)

(52) U.S. Cl.
CPC ............. *G01P 15/097* (2013.01); *B81B 3/0021* (2013.01); *B81B 2203/0118* (2013.01);
(Continued)

(58) Field of Classification Search
USPC ...................... 73/514.29, 514.33, 579, 862.59
See application file for complete search history.

(56) References Cited

U.S. PATENT DOCUMENTS

2003/0104648 A1*  6/2003  Rudhard et al. ................ 438/50
2005/0150280 A1   7/2005  Tang et al.
(Continued)

FOREIGN PATENT DOCUMENTS

JP          61-239644 A       10/1986

OTHER PUBLICATIONS

French Preliminary Search Report issued Feb. 10, 2010 in Patent Application No. FR 0954998 with English Translation of Category of Cited Documents.
(Continued)

*Primary Examiner* — John Chapman, Jr.
(74) *Attorney, Agent, or Firm* — Oblon, McClelland, Maier & Neustadt, L.L.P.

(57) ABSTRACT

A nano electro-mechanical system (NEMS) formed on a substrate is provided including at least one fixed part associated with the substrate and at least one movable part in relation to the substrate, the system including a transduction component configured to excite the movable part to confer on it a movement and/or to detect a movement of the movable part, the transduction component including at least one electrically conductive material. The electrically conductive material is made of an AlSi alloy based deposition, the deposition being supported at least in part by the movable part of the system.

13 Claims, 12 Drawing Sheets

(51) Int. Cl.
*B81B 3/00* (2006.01)
*G01N 29/02* (2006.01)
*G01P 15/12* (2006.01)

(52) U.S. Cl.
CPC ......... *B81B2203/058* (2013.01); *G01N 29/022* (2013.01); *G01N 2291/014* (2013.01); *G01N 2291/0427* (2013.01); *G01P 15/123* (2013.01)

(56) References Cited

U.S. PATENT DOCUMENTS

2008/0314148 A1* 12/2008 Robert ................. 73/514.33
2009/0084167 A1    4/2009 Djakov et al.
2009/0139330 A1*  6/2009 Pavelescu et al. ......... 73/514.32
2009/0289747 A1* 11/2009 Duraffourg et al. ....... 333/219.2

OTHER PUBLICATIONS

Otto J. Gregory et al., "Effect of Alumnium Doping on the High-temperature Stability and Piezoresistive Response of Indium Tin Oxide Strain Sensors", Thin Solid Films, Elsevier-Sequoia S.A. Lausanne, CH, vol. 476, No. 2, XP004752390, Apr. 8, 2005, pp. 344-351.
Mo Li et al., "Ultra-sensitive NEMS-based Cantilevers for Sensing, Scanned Probe and Very High-frequency Applications", Nature Nanotechnology Nature Publishing Group UK, vol. 2, No. 2, XP002567868, Feb. 2007, pp. 114-120.
I. Bargatin et al., "Efficient electrothermal actuation of multiple modes of high frequency nanoelectromechanical resonators", Applied Physics Letters, vol. 90, 2007, 3 pages.
R. L. Parker et al., "Electrical resistance-strain characteristics of thin evaporated metal films", Journal of Applied Physics, vol. 34, No. 9, Sep. 1963, pp. 2700 to 2708 and Cover page.
Jih-Fen Lei et al.,"Thin-film thermocouples and strain-gauge technologies for engine applications", Sensors and Actuators A: Physical, vol. 65, No. 2-3, Mar. 15, 1998, pp. 187-193.
H. Chiriac et al.,"Ni—Ag thin films as strain-sensitive materials for piezoresistive sensors", Sensors and Actuators A: Physical, vol. 76, No. 1-3, 1999, pp. 376-380.
R.R. Desai et ai., "Indium sesquitelluride (In2Te3) thin film strain gauge", Sensors and Actuators A: Physical, vol. 121, No. 2, 2005, pp. 405-409.
K.L. Ekinci et al., "Ultimate limits to inertial mass sensing based upon nanoelectromechanical systems", Journal of Applied Physics, vol. 95, No. 5, 2004, pp. 2682 to 2689.
X.L. Feng et al.,"A self-sustaining ultrahigh-frequency nanoelectromechanical oscillator", Nature Nanotechnology, vol. 3, No. 6, Jun. 2008, pp. 342 to 346.
N. Yazdi et al., "Micromachines inertial sensors", Proceedings of the IEEE, vol. 86,No. 8, Aug. 1998, pp. 1640 to 1659.
Jih-Fen Lei, "Advances in Thin Film Sensor Technologies for Engine Applications", NASA Technical Memorandum, 1997,8 pages.

* cited by examiner

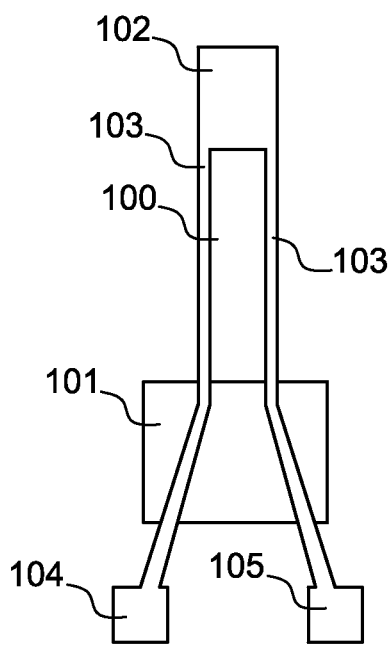 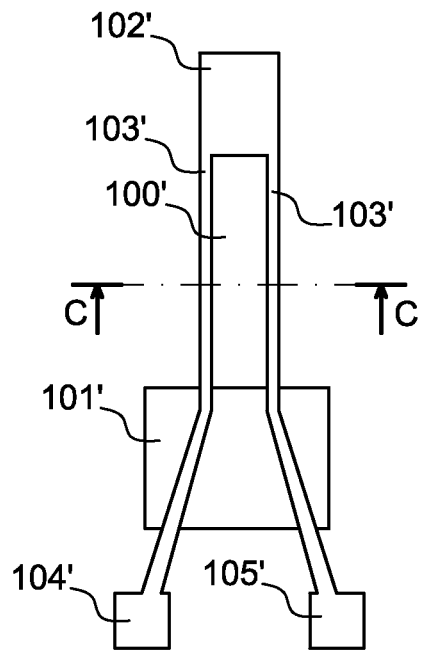
FIG. 14A  FIG. 14B
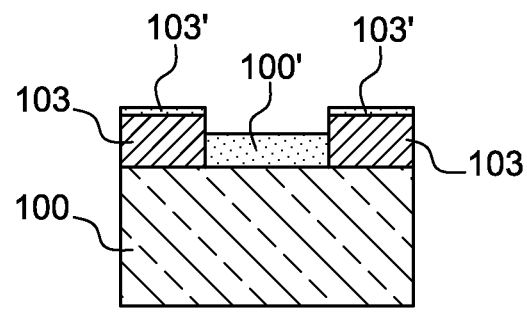
FIG. 14C

NEMS COMPRISING ALSI ALLOY BASED TRANSDUCER

CROSS-REFERENCE TO RELATED APPLICATION

This application is a national phase application based on PCT/EP2010/060033, filed on Jul. 13, 2010, which claims the benefit of U.S. Provisional Application No. 61/226,419, filed on Sep. 17, 2009. This application is also based upon and claims the benefit of priority under 35 U.S.C. §119 from prior French Patent Application No. 09 54998, filed on Jul. 17, 2009. The entire contents of each of the above applications are incorporated herein by reference.

TECHNICAL FIELD

The invention relates to devices known as NEMS (for "Nano Electro-Mechanical Systems") comprising at least one movable part associated with transduction means (of excitation and/or detection).

STATE OF THE PRIOR ART

The development of NEMS necessitates developing integrable actuation and detection principles, adapted to detecting slight deformations at high frequencies compared to the displacements and frequencies brought into play in microsensors, produced by MEMS (for "Micro Electro-Mechanical Systems") technologies. The principles available must make it possible to design simple patterns and production methods. The techniques implemented must remain compatible with the tools and methods of microelectronics so that their very large scale integration, via clean rooms or microelectronic foundries, is accessible. In this spirit, the pertinence of the principles of thermoelastic actuation and piezoresistive detection has been demonstrated. Reference may be made in this respect to the article "Ultra-sensitive NEMS-based cantilevers for sensing, scanned probe and very high-frequency applications" of Mo Li et al., Nature Nanotechnology, Volume 2, N° 2, pages 114 to 120, 2007.

Concerning the thermoelastic actuation (bimetal effect), in order to limit the consumption and to guarantee the optimal efficiency of the actuator, materials with TEC (thermal expansion coefficient) as different as possible must be chosen. Reference may be made in this respect to the article "Efficient electrothermal actuation of multiple modes of high-frequency nanoelectromechanical resonators" of I. Bargatin et al., Applied Physics Letters, 2007, 90(9), 93116.

For piezoresistive detection, materials having high gauge factors with a resistivity as low as possible are sought in order to reduce the problems linked to Johnson noise. Said noise is a white noise linked to the value of the resistance and the spectral density of which is given by:

$$B = \sqrt{4kTR} \text{ expressed in } V/\sqrt{Hz} \tag{1}$$

where k=Boltzmann's constant, T=temperature and R=overall resistance.

The variation in resistance ΔR, linked to the variation in strain (σ) induced by the deformation of the material (ΔR being proportional to the strain), may be known.

A resistance formed by an elastic conducting structure in the shape of a bar varies as a function of an axial strain as follows:

$$\frac{dR}{R} = \frac{d\rho}{\rho} + \frac{dL}{L} + \frac{dS}{S} = \frac{d\rho}{\rho} + \varepsilon_L(1 + 2v) \tag{2}$$

$\rho$ is the resistivity of the elastic bar, $\varepsilon_L$ is the relative elongation of the material (S and L are respectively the section and the length of the bar). $v$ is the Poisson coefficient.

The first term corresponds to the piezoresistive effect strictly speaking whereas the second corresponds to a purely geometric effect. In the case of a semi-conductor such as silicon, the second term is of several orders of magnitude less than the first. Piezoresistivity is a physical phenomenon that links this variation in resistivity to a strain applied to the gauge. This relation may be expressed as follows:

$$\frac{d\rho}{\rho} = \Pi_L \sigma_L + \Pi_T \sigma_T \tag{3}$$

where $\Pi_L = \Pi_{11} - 2(\Pi_{11} - \Pi_{12} - \Pi_{44})(l_1^2 m_1^2 + l_1^2 n_1^2 + m_1^2 n_1^2)$ $\Pi_T = \Pi_{12} + (\Pi_{11} - \Pi_{12} - \Pi_{44})(l_1^2 l_2^2 + m_1^2 m_2^2 + n_1^2 n_2^2)$ $\Pi_{ij}$ are the elements of the piezoresistivity tensor expressed along the main crystalline axes of the semi-conductor. $\Pi_L, \Pi_T$ are respectively the longitudinal and transversal piezoresistive coefficients expressed in the principal mark of the gauge (N, T). $\sigma_L$ and $\sigma_T$ are respectively the longitudinal and transversal strains applied. This is represented in FIG. 1, which is a diagram of a piezoresistive gauge and associated principal axes (N, T). $l_i$, $m_i$ and $n_i$ are the coordinates of the director vectors T and N in relation to the crystalline base of the material. In the case of a purely metal gauge, $$\frac{d\rho}{\rho}$$

is zero. The variation in resistance is then purely induced by the elongation of the material and amounts to:

$$\frac{dR}{R} = \varepsilon_L(1 + 2v) = \gamma \varepsilon_L \tag{4}$$

In this precise case, $\gamma$ (known as the gauge factor) is of the order of several units (see table 1 and FIG. 1).

In the case of a semi-conducting gauge, the equation (3) can also amount to a form equivalent to (4) using Hooke's law. In this case, $\gamma$ is between 50 and 200, depending on the type of doping and the crystalline axes considered. Table 1 gives some examples of gauge factor for commonly used alloys used and silicon.

TABLE 1

| Materials | Gauge factor | | Final elongation (%) |
| --- | --- | --- | --- |
| | Low deformation | High deformation | |
| Copper | 2.6 | 2.2 | 0.5 |
| Constantan | 2.1 | 1.9 | 1.0 |
| Nickel | −12 | 2.7 | — |
| Platinum | 6.1 | 2.4 | 0.4 |
| Silver | 2.9 | 2.4 | 0.8 |
| 40% gold/palladium | 0.9 | 1.9 | 0.8 |
| Semiconductor | ~100 | ~600 | — |

Constantan is an alloy of copper and nickel $Cu_{60}Ni_{40}$, similar to the annealed alloys of copper and nickel called "Ferry", "Advance" and "Copel". The gauge factor of a semiconductor material largely depends on its level of doping and on its doping species.

FIG. 2 is a diagram illustrating, for several metallic materials, the variation in resistance in % ΔR/R as a function of the percentage deformation D of these materials. In this diagram, the gauge factor for a material is the slope of the corresponding curve. Curve 1 has been drawn for the alloy 10% rhodium/platinum, curve 2 for the alloy "Ferry", curve 3 for constantan, curve 4 for the alloy 40% gold/platinum and curve 5 for nickel. It may be seen that for small deformations, the gauge factor of nickel is negative.

FIG. 3 is taken from the document "Electrical resistance-strain characteristics of thin evaporated metal films" of R. L. Parker et al., Journal of Applied Physics, Vol. 34, N° 9, September 1963, pages 2700 to 2708. This figure represents the gauge factor γ as a function of the resistance $R_s$ of a layer of aluminium. It may be observed that the gauge factor for aluminium alone can become negative for certain resistance values (see zone A), in other words for certain geometric parameters.

At the scale of microsystems (MEMS), for piezoresistive detection, metallic materials have little by little been abandoned in favour of doped semi-conducting gauges (P- or N-type Si). As mentioned previously, the gauge factors in intrinsic Si are much higher (several hundreds) than in the case of metal materials (between 2 and 4). Since intrinsic silicon is too resistive, it is doped in order to make it more conductive. In doing so, the gauge factor decreases but remains all the same around 100 for doping levels close to $10^{19}$ cm$^{-3}$, in other words for doping ranges among the highest commonly used in microelectronics. At such levels, the resistivity of the material is of the order of 10 mΩ.cm. This value is markedly higher than those measured in several conventional metals (Au, Cu, etc.), which is of the order of several μΩ.cm. This value makes it possible to have higher polarisation voltages of gauges and thereby to obtain an output signal all the stronger. At the same time, for microsystems applications the noise inherent in the resistance remains well below the output signals.

Apart from the high signals thanks to the high gauge factors, the fact of being able to work from semi-conducting gauges makes it possible to envisage production methods perfectly compatible with those of microelectronics.

For NEMS based mass sensor applications (for example multi-gas platforms or mass spectrometers), the use of metal layers as sensitive piezoresistive component becomes advantageous. Indeed, the semi-conducting gauges at the scale of a NEMS sensor have very small typical sections (of the order of 0.2 nm$^2$). In considering a typical doping of $10^{18}$ cm$^{-3}$ conventionally used in MEMS technology, their resistances have high unit length values, which makes the measurement very awkward (reduction of the signal by resistive bridge effect for example). It is then necessary to highly dope the gauge beyond $10^{19}$ cm$^{-3}$, which strongly reduces the gauge coefficient value.

Furthermore, it is shown that the mass resolution is proportional to the noise density of the gauge and inversely proportional to the detection gain of said gauge given to the first order by the product reading voltage, gauge factor. Given the high resistivities and lower gauge value of semi-conducting gauges, the resolution drops to values close to those obtained with metal sensitive layers.

In addition, for mass spectrometry applications, the ambient temperature may be low, of the order of 50 K. At these temperatures, there exists an effect known as "carrier freeze-out" in semi-conductors increasing very considerably their resistivity. The use of semi-conducting gauges for this application is thus disadvantageous compared to metal layers.

This observation for NEMS applications has already been published and productions from different metals have thus been undertaken with excellent results (see the article of Mo Li et al. cited above). Nevertheless, the use of the latter such as gold can pose several production problems, such as the steps of etching or the non compatibility of these metals with CMOS procedures due to their highly contaminating character.

Apart from the metals and metallic alloys presented in FIG. 2 and in table 1 of layers of PdCr, PdCr/Pt (see the article "Thin-film thermocouples and strain-gauge technologies for engine applications" of Jih-Fen Lei et al., Sensors and Actuators A: Physical, Vol. 65, N$^{os}$ 2-3, 15 March 1998, pages 187 to 193), $Ni_xAg_{1-x}$ layers (see H. Chiriac et al., "Ni—Ag thin films as strain-sensitive materials for piezoresistive sensors'", Sensors and Actuators A: Physical, Vol. 76, N$^{os}$ 1-3, pages 376 to 380) or more exotic layers such as $In_2Te_3$ (see R. R. Desai et al., "Indium sesquitelluride ($In_2Te_3$) thin film strain gauge", Sensors and Actuators A: Physical, Vol. 121, N° 2, 2005, pages 405 to 409) for MEMS. These materials could be integrated for the production of NEMS but they are for the most part "exotic" metals (Ag, Pt, Pd, etc.) for CMOS compatible collective production methods. These metals are generally contaminants when they are etched.

In the document US 2005/0150280, aluminium or a metallic alloy based on aluminium are proposed as potentially interesting layer. Nevertheless, those skilled in the art know that aluminium deposited without precaution on silicon migrates into the semiconductor. Thus, the invention proposes forming an alloy based on aluminium integrating silicon (in typical proportions between 1% and 2%) to avoid the problems of migration. The alloy AlCuSi is also used not only to avoid the eutectic but also to limit the effects of electromigration of the aluminium into the silicon and inversely when a rise in temperature induced by Joule effect in the current loop becomes significant.

This AlSi alloy has been used for interconnection applications in microelectronics in the 1970s. Reference may be made in this respect to the document JP-A-61-239 644. The materials AlSi and AlCuSi have never, on the other hand, been considered as materials suited to being used in thin film to form a piezoresistive transduction.

DESCRIPTION OF THE INVENTION

Like any metal, the gauge factor of an aluminium alloy based material is low and its resistivity is very low. In other words, that signifies that the signal applied to a sensitive component based on aluminium alloy must be very weak to avoid any fusion of the component by fusible effect. Furthermore, the transduction is not very efficient due to its low gauge factor. Since the displacements and the strains in the movable mechanical components of the microsystems are high, all of these arguments incite those skilled in the art to rule out this type of layer to form the sensitive layer.

For low deformation NEMS applications (compared to its smallest dimension) that cannot in essence accept high powers (thus high voltages), these arguments become prejudices. The sensitivity of a NEMS (particularly its capacity to be sensitive to a mass settling on its surface or to an acceleration) is no longer the major problem (in particular for frequency detection sensors). Consequently, the determination of the sensitive layer will be made rather on considerations of background noise, of integration to limit any parasitic action on the signal. Metal layers thus become good candidates. In addition, the aluminium alloy based layer has a large difference of thermal expansion coefficient compared to silicon, which also makes it possible to carry out a thermoelastic actuation simultaneously to the detection.

Frequency detection consists in measuring any shift in the mechanical resonance frequency of an oscillating component when it is subjected to a given stimulus. In the case of the invention, it involves measuring a frequency shift when a very small mass settles on the surface of the sensitive component. The size of the NEMS is thus favourable to attain high sensitivities. At the same time, the mechanical frequencies attained with these nano-structures are high (100 MHz and above). It is thus advantageous that the input impedances of the sensor and the electrical circuits are close and adapted 50 Ω.

To resume, contrary to the prejudices existing in those skilled in the art and specialists of MEMS sensors, the choice of a thin film of aluminium alloy, to form both the piezoresistive sensitive layer and the thermoelastic actuation layer in mass sensors on NEMS, is the most adapted. It meets in fact all of the requisite conditions: low resistivity, high difference of CTE with silicon (constituting the base material of NEMS), low mass density, deposition in thin films, uniform and controllable, easy to implement, compatibility with CMOS and other microelectronic methods (VLSI).

Due to the steps of release at the end of implementation, the material must also resist the techniques of etching of the sacrificial layer achieving the release making it possible to obtain the movable part (for example, etching based on HF).

Furthermore, a low mass density of the material is also sought for mass sensor applications where it has been demonstrated that the resolution of the sensor is proportional to its total mass. The lighter the thermoelastic actuation layer and the sensitive layer, the finer the final resolution of the system will be.

From the above requirements definition, it is possible to define a list of CMOS compatible materials capable of meeting the listed requirements. The inventors of the present invention have studied numerous possibilities of use of materials compatible with a CMOS foundry and making it possible to form both the sensitive piezoresistive layer and the thermoelastic actuation layer of NEMS sensors. Among these materials, may be cited the following: PtSi, NiSi, $TiSi_2$, AlSi, $WSi_2$, TiN, TiN/Cu, Cu, Ti, Cr, Ni and W.

Among all these materials, the inventors have retained AlSi alloy based materials, material used conventionally for the interconnection known as "back-end" (operations downstream of a production method) in CMOS technology in the 1980s.

The object of the invention is thus a Nano ElectroMechanical System (NEMS) comprising at least one fixed part associated with a substrate and at least one movable part in relation to the substrate, said system comprising transduction means capable of exciting the movable part to confer on it a movement and/or to detect a movement of the movable part, the transduction means comprising at least one electrically conductive material, characterised in that the electrically conductive material is formed of an AlSi alloy based deposition, said deposition being supported at least in part by the movable part of the system.

The AlSi alloy based deposition may be an alloy chosen among AlSi and AlCuSi. The alloy of AlSi is particularly advantageous, particularly for technological implementation reasons (limited number of steps).

The transduction means may further comprise, under the electrically conductive material, an additional layer to structure the electrically conductive material and/or to amplify the movement detected and/or to form a barrier to the diffusion of the conductive material. This additional layer may be a layer of Ti or Ti/TiN.

The AlSi alloy based deposition may form at least one current loop for the excitation of the movable part and/or for the detection of a movement of the movable part. It can form two overlapping current loops, one for the excitation of the movable part and the other for the detection of a movement of the movable part.

The movable part of the system may comprise a clamped-free beam or a clamped-clamped beam. Obviously, other shapes of movable part may be used such as for example a plate, a disc, a ring, a coil, etc. and anchored by at least one anchoring point to the substrate.

The substrate may comprise a support covered successively with an electrically insulating layer and a superficial silicon layer, said fixed and movable parts being formed in the superficial silicon layer, the movable part being obtained thanks to a hollowing out formed in the electrically insulating layer.

According to one embodiment, the system further comprising a test mass, the movable part is attached by one of its ends to the substrate and by its other end to the test mass, the transduction means being means capable of detecting a movement.

According to another embodiment, the system further comprising a test mass, a resonator connects the test mass to the substrate, the movable part being attached by one of its ends to the substrate and by its other end to the resonator, the transduction means being means capable of detecting an acceleration.

The AlSi alloy based deposition may have a thickness between 10 and 100 nm, preferably between 40 and 80 nm.

The system may further comprise at least one deposition of an electrografted functionalization layer, beyond the AlSi alloy based material.

The NEMS according to the invention may apply to the production of a sensor chosen among a mass sensor, a gas sensor, a biochemical sensor, a force sensor, an inertial sensor and a pressure sensor.

Advantageously, the AlSi alloy according to the invention comprises between 0.5% and 4% of silicon by weight and preferentially 1%. The maximum quantity of materials, mixed with aluminium in the alloy, is determined by the limit of solubility of these materials in this alloy, as a function of the maximum temperature used in NEMS production methods.

BRIEF DESCRIPTION OF DRAWINGS

The invention will be better understood and other advantages and particularities will become clear on reading the following description, give solely by way of example and non limiting, and by referring to the appended drawings, among which:

FIG. 14C is a sectional view along the axis C-C of FIG. 14B.

DETAILED DESCRIPTION OF SPECIFIC EMBODIMENTS OF THE INVENTION

Several examples of producing structures for mass sensors (mass spectrometry, chemical sensors, biochemical sensors) will now be described. These examples are formed, for example, on an SOI substrate having a superficial silicon layer of 160 nm thickness resting on a buried silicon oxide layer of 400 nm thickness. On the superficial silicon layer, for example, a layer of AlSi from 40 to 80 nm thickness is deposited.

Figure 4:
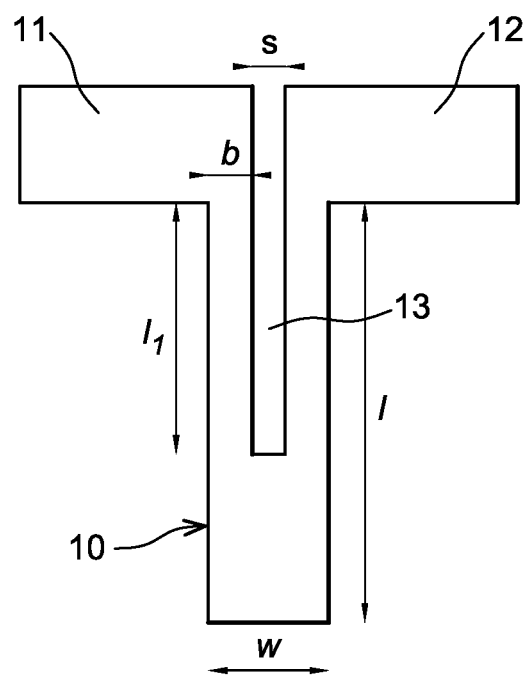
FIG. 4 is a top view of a clamped-free beam bearing a current loop common to thermoelastic actuation and to piezoresistive detection, according to the invention.

FIG. 4 is a top view of a clamped-free beam (or cantilever beam) bearing a current loop common to thermoelastic actuation and to piezoresistive detection. The beam 10 is fixed to the substrate by parts 11 and 12 and is overhanging from these parts. The current loop is defined from the parts 11 and 12 by an interval 13. Table 2 gives examples of dimensions (in μm) for such a beam.

TABLE 2

| l | w | $l_1$ | b | s |
|---|---|---|---|---|
| 1.5 | 0.6 | 0.5 | 0.2 | 0.2 |
| 2.8 | 0.7 | 1 | 0.25 | 0.2 |
| 5 | 1 | 2 | 0.3 | 0.4 |

Figure 5A:
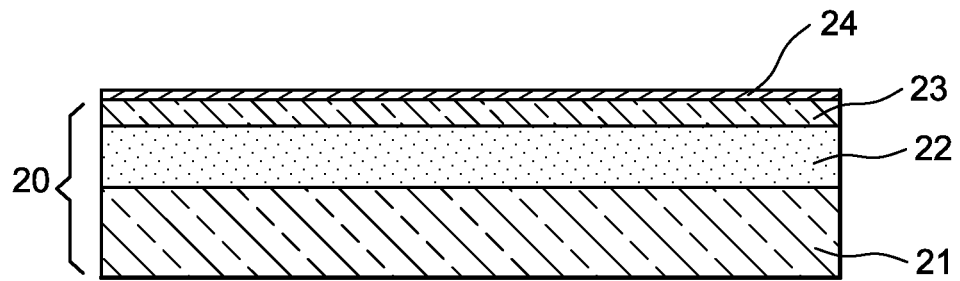
FIGS. 5A to 5C are longitudinal sectional views illustrating a method of producing the clamped-free beam of FIG. 4, FIGS. 6 and 7 are top views of clamped-free beams bearing a current loop dedicated to thermoelastic actuation and a current loop dedicated to piezoresistive detection, according to the invention.
Figure 5B:
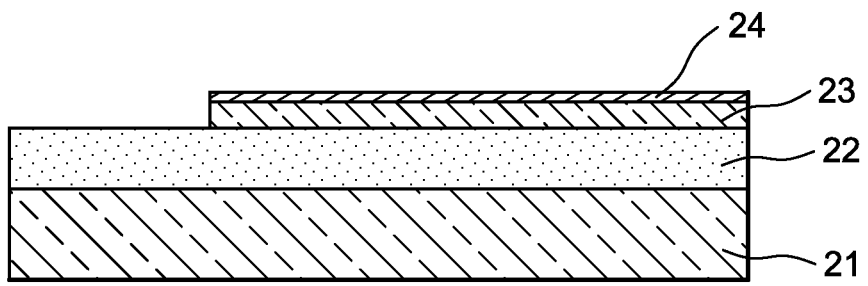
Figure 5C:
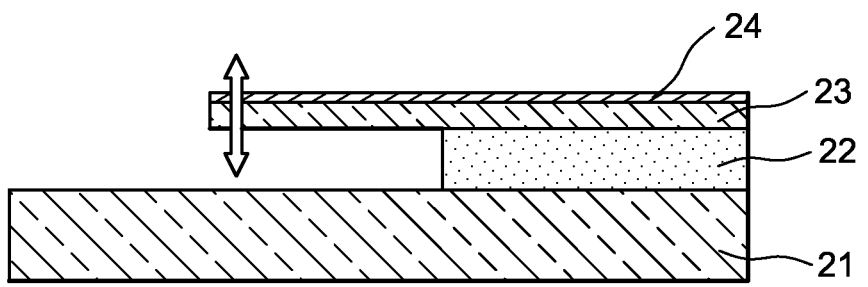

FIGS. 5A to 5C are longitudinal sectional views illustrating a method of producing the clamped-free beam of FIG. 4.

FIG. 5A shows an SOI substrate 20 constituted of a silicon support 21 supporting successively a buried oxide layer 22 and a superficial silicon layer 23. An AlSi layer 24 of 50 nm thickness is formed on the superficial layer 23.

The definition of the electrically conductive part of the beam on the superficial layer 23 is then carried out by photolithography and etching for example by chlorinated plasma such as $BCl_3$. Then, the etching of the superficial silicon layer 23 is carried out by a gaseous mixture comprising for example $CF_4$. The structure represented in FIG. 5B is obtained.

It remains to release the beam. This is done by etching of the buried oxide layer 22 using HF. The structure represented in FIG. 5C is obtained, where the direction of displacement of the beam is indicated by an arrow.

Figure 6:
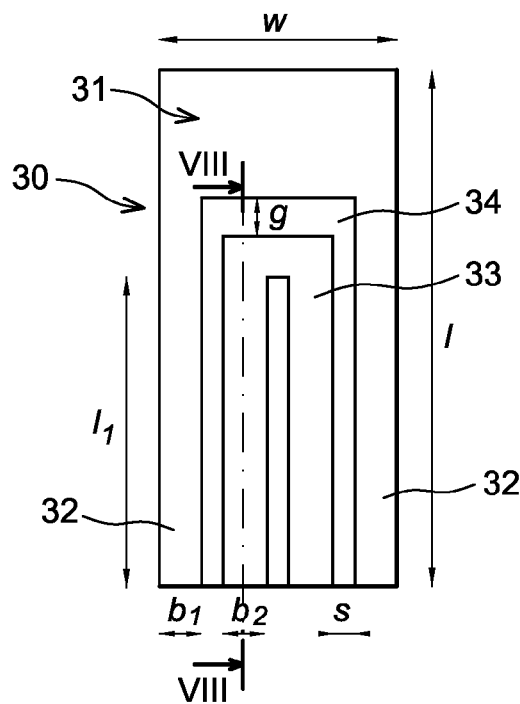
Figure 7:
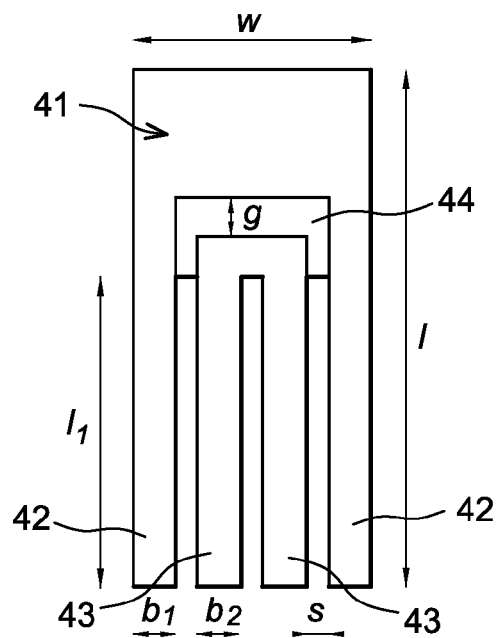

FIGS. 6 and 7 are top views of two clamped-free beams bearing a current loop dedicated to thermoelastic actuation and a current loop dedicated to piezoresistive detection, the loops being overlapping. These beams are symmetrical in relation to their longitudinal axis. The part of the beam situated at the top of each figure is free. The part of the beam situated at the bottom of each figure is embedded.

FIG. 6 shows a beam 30 comprising one end 31 capable of moving in a direction perpendicular to the figure plane, a first current loop 32 made of AlSi and a second current loop 33 made of AlSi. In this embodiment example, all of the current loops rest on a silicon layer 34.

FIG. 7 shows a beam 40 comprising one end capable of moving in a direction perpendicular to the figure plane, a first AlSi current loop 42 and a second AlSi current loop 43. In this embodiment example, only the parts of the current loops situated towards the end 41 rest on a silicon layer 44.

Table 3 gives examples of dimensions (in μm) for the beams represented in FIGS. 6 and 7.

TABLE 3

| l | w | $l_1$ | $b_1$ | $b_2$ | s | g |
|---|---|---|---|---|---|---|
| 5 | 1.4 | 2 | 0.2 | 0.2 | 0.2 | 1 |
| 7 | 2.1 | 2.5 | 0.3 | 0.3 | 0.3 | 1.5 |

FIGS. 8A to 8D are longitudinal sectional views illustrating a method of producing the clamped-free beam of FIG. 6. These figures are views along the axis VIII-VIII of FIG. 6.

Figure 8A:
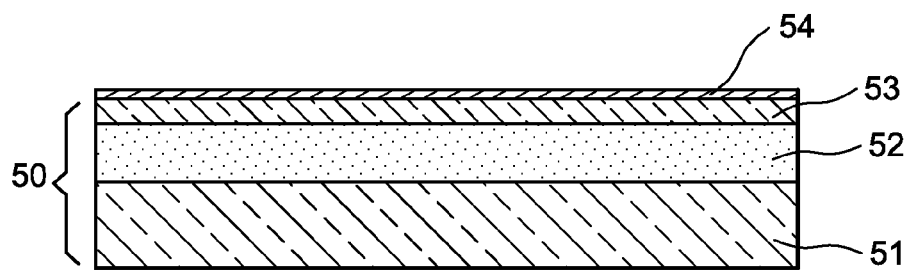
FIGS. 8A to 8D are longitudinal sectional views illustrating a method of producing the clamped-free beam of FIG. 6, FIG. 8D' is a longitudinal sectional view showing an alternative embodiment of a clamped-free beam.

FIG. 8A shows an SOI substrate 50 constituted of a silicon support 51 supporting successively a buried oxide layer 52 and a superficial silicon layer 53. An AlSi layer 54 of 50 nm thickness is formed on the superficial layer 53.

Figure 8B:
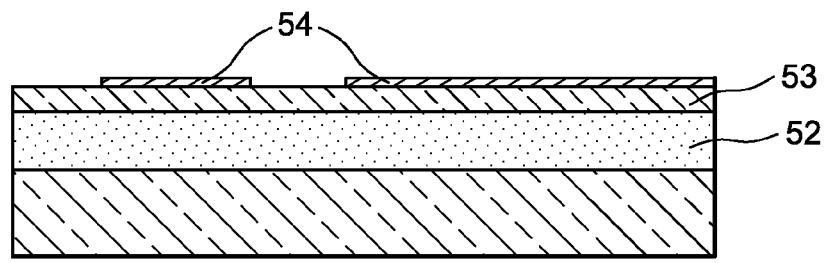
Figure 8C:
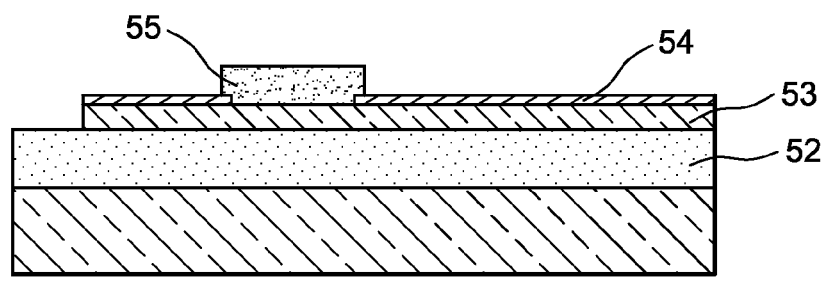

The definition of the electrically conductive part of the beam on the superficial layer 53 is then carried out by lithography and etching. This is represented in FIG. 8B.

The definition of the silicon part of the beam is then carried out. To do this, a step of lithography is carried out to leave a protection pad 55 on the part of the superficial silicon layer 53 not covered by the remaining AlSi layer 54 and which is to be conserved (see FIG. 8C). The etching of the superficial silicon layer 53 is then carried out by a $CF_4$ based plasma.

Figure 8D:
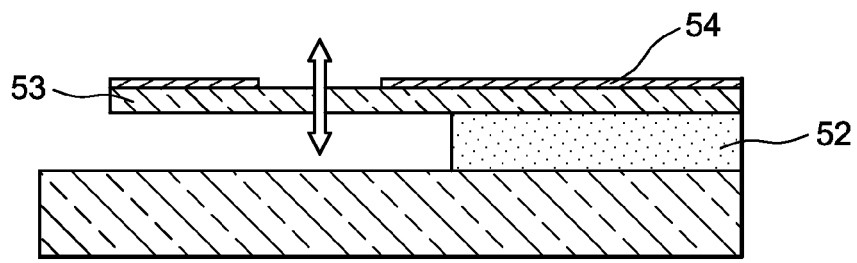
Figure 8D:
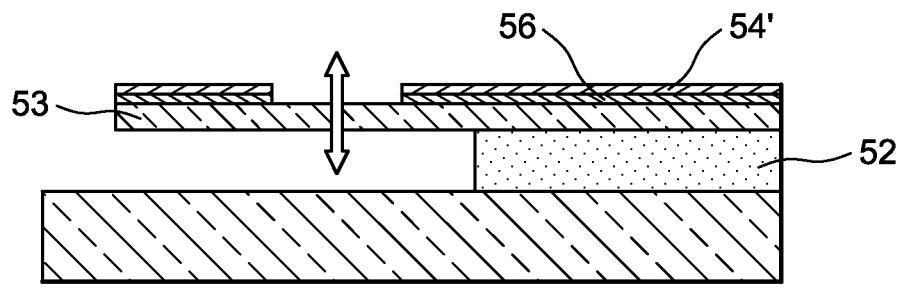

The protection pad 55 is eliminated and the release of the beam is carried out by HF etching of the buried oxide layer 52. The structure represented in FIG. 8D is obtained, where the direction of displacement of the beam is indicated by an arrow.

Figure 9:
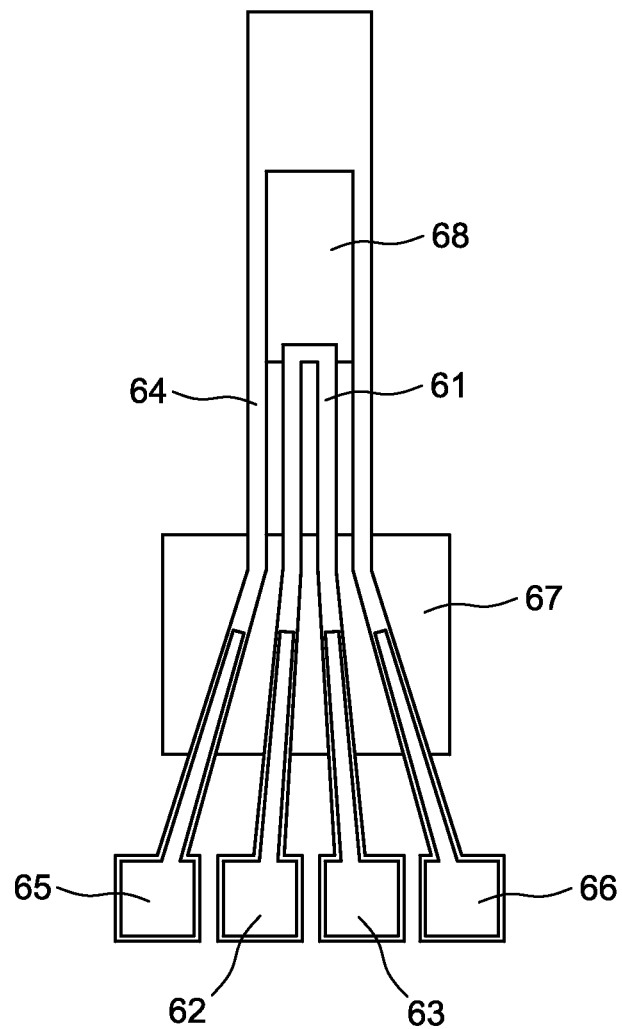
FIG. 9 is a top view of another clamped-free beam bearing a current loop dedicated to thermoelastic actuation and a current loop dedicated to piezoresistive detection, according to the invention.

FIG. 9 is a top view of another clamped-free beam bearing a current loop dedicated to thermoelastic actuation and a current loop dedicated to piezoresistive detection. The beam comprises an actuating electric loop 61 connected to the connection pads 62 and 63 and an electric detection loop 64 connected to the connection pads 65 and 66. The embedment area of the beam is shown under the reference 67. The reference 68 designates a part of thin silicon film remaining under the free part of the beam.

Furthermore, it is also possible to duplicate the structures described above in network in a VLSI approach to obtain a network of silicon nano-beams with depositions of AlSi.

It is also possible to add under the deposition of AlSi one or more layers of metal or other material to structure the AlSi layer or to amplify the deformation of the upper sensitive layer and thus to amplify the output electrical signal and/or again to play the role of barrier to the diffusion of the aluminium alloy into the rest of the structure. This mechanical amplification is due to a simple effect of leverage because the median plane of the sensitive AlSi layer is raised in relation to the neutral line of the silicon part of the beam. FIG. 8D' illustrates such a structure where a layer 56, for example of Ti or Ti/TiN, is provided under the AlSi layer 54'.

Any architecture enabling an electrical continuity may be envisaged. Thus, instead of considering clamped-free beams (or cantilevers), bridges (clamped-clamped beams) may be considered.

Figure 10A:
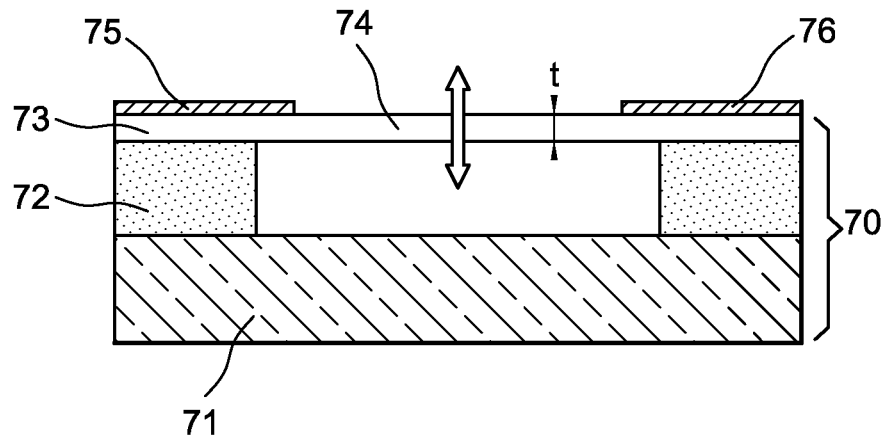
FIGS. 10A and 10B are respectively longitudinal sectional views and top views of a clamped-clamped beam with an actuation loop to one embedment and a detection loop to the other embedment, according to the invention.
Figure 10B:
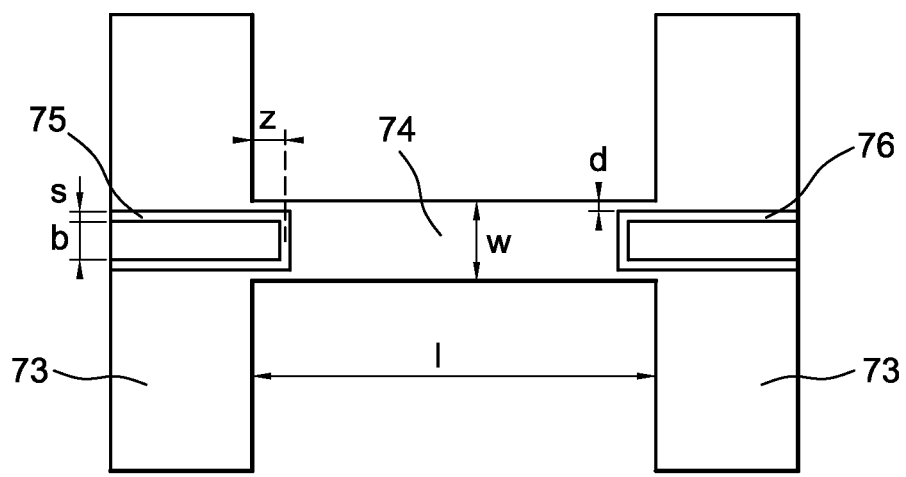

FIGS. 10A and 10B are views respectively in longitudinal section and top section of a clamped-clamped beam with an actuation loop to one embedment and a detection loop to the other embedment.

The structure shown in FIGS. 10A and 10B is formed from an SOI substrate 70 comprising a support 71 supporting successively a buried oxide layer 72 and a superficial silicon layer 73. The part 74 of the beam, made of silicon, is obtained by photolithography and by plasma etching of the superficial silicon layer then by HF etching of the buried oxide layer 72. Depositions of AlSi are formed on the beam to obtain an actuation loop 75 to one of the embedments and a detection loop 76 to the other embedment.

Table 4 gives examples of dimensions (in μm) for the clamped-clamped beam represented in FIGS. 10A and 10B.

TABLE 4

| l | w | b | s | z | d | $f_o$ |
|---|---|---|---|---|---|---|
| 1 | 0.34 | 0.08 | 0.05 | 0.22 | 0.08 | 1 400 |
| 1.1 | | | | 0.25 | | 1 156 |
| 1.2 | | | | 0.27 | | 972 |
| 1.3 | | | | 0.29 | | 828 |
| 1.5 | 0.34 | 0.08 | 0.05 | 0.34 | 0.08 | 622 |

TABLE 4-continued

| l | w | b | s | z | d | $f_o$ |
|---|---|---|---|---|---|---|
| 2 | 0.34 | 0.08 | 0.05 | 0.45 | 0.08 | 350 |
| 2.5 | 0.34 | 0.08 | 0.05 | 0.56 | 0.08 | 224 |
| 3.5 | 0.34 | 0.08 | 0.05 | 0.46 | 0.08 | 114 |

This table moreover gives the values of the resonance frequency of the beam (in MHz).

It is also possible to envisage movements in the plane of the substrate unlike all of the examples given previously. In this case, the AlSi metallic gauge is compressed or expanded as a function of a beam that is connected to it (see FIG. 11). This detection model has been disclosed in the document FR-A-2 917 731. In this case, the active part of the gauge according to the present invention is not made of silicon. Silicon is only a non-conducting, or weakly conducting, mechanical support compared to the deposited AlSi metallic layer. The gauge is thus the layer of AlSi. If the gauge factor is in this case lower, the Johnson white noise induced by the gauge is on the other hand much weaker, which makes it possible to improve the intrinsic resolution of the sensor.

Figure 11:
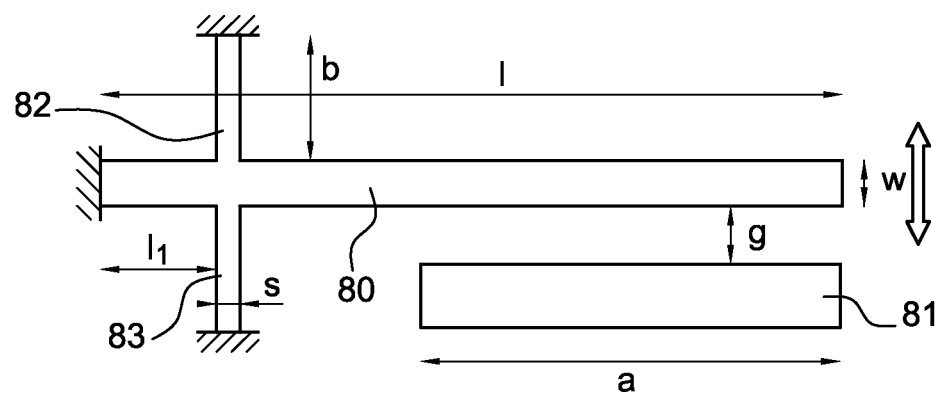
FIG. 11 is a schematic representation, in top view, of a structure comprising a clamped-free beam capable of moving in the plane of its support substrate, according to the invention.

FIG. 11 schematically represents such a structure in top view. It shows a movable beam 80 embedded in the substrate by one of its ends, the other end being free. Parallel to the movable beam 80 and on the side of its free end is found an actuating electrode 81. Perpendicularly to the movable beam 80 and on the side of its embedded end are found two piezoresistive gauges 82 and 83, each being attached on the one side to the movable beam 80 and on the other side to the substrate. The movable beam 80, the actuation electrode 81 and the piezoelectric gauges 82 and 83 are made of silicon covered with AlSi. The double arrow indicates the direction of displacement of the movable beam 80.

Table 5 gives examples of dimensions (μm) for the structure represented in FIG. 11.

TABLE 5

| l | W | $l_1$ | b | s | a | g |
|---|---|---|---|---|---|---|
| 6 | 0.1 | 3 | 0.2 | 0.08 | 4 | 0.2 |
| 6 | 0.1 | 3 | 0.5 | 0.08 | 4 | 0.2 |
| 6 | 0.2 | 3 | 0.2 | 0.08 | 4 | 0.1 |

Several types of depositions may be envisaged at different thicknesses. Different compositions can also be obtained, for example AlSi of 1% aluminium-silicon type. A first deposition is carried out by sputtering at a temperature of 175° C. The AlSi layer formed may be formed either via a continuous deposition at constant power, or in several steps, for example in two stages, according to the requisite thickness. A first layer of several tens of nanometres may be deposited with a power of 3 kW for example (or 1.5 kW), enabling a quite dense and quite uniform (from 20 to 40 nm) layer to be obtained. A second layer may then be added at low power (for example 0.5 kW) in order to better control the final thickness (50 to 60 nm in the end).

High temperature depositions make it possible to reveal preferential crystalline orientations of the AlSi grains.

A second type of deposition may also be carried out via a low temperature method at 20° C. for example. This makes it possible to obtain smaller grains of AlSi and finer discontinuities between grains with a more homogeneous distribution. These low temperature depositions also make it possible to reduce the roughness of the films of AlSi (by a factor 5, around 1 nm rms in other words root mean square) but increase the resistivity of the material (0.5 to 1 µohm.cm) at constant thickness.

Variable thicknesses can be obtained. For example, the feasibility of uniform and continuous depositions up to 10 nm at least has been demonstrated experimentally. Thicknesses of 80 nm have also been obtained on NEMS. Higher thicknesses may be deposited (100 nm, 200 nm, 500 nm) but it is aimed rather to favour thin films (range from 10 to 100 nm).

Characterisations of resonators such as those described in FIG. 4 have been realised by using films of AlSi of 80 nm thickness as component simultaneously of thermoelastic actuation and piezoresistive detection. The results of the resonance curves are given in FIGS. 12 and 13. These results conform to the theoretical predictions.

Figure 12:
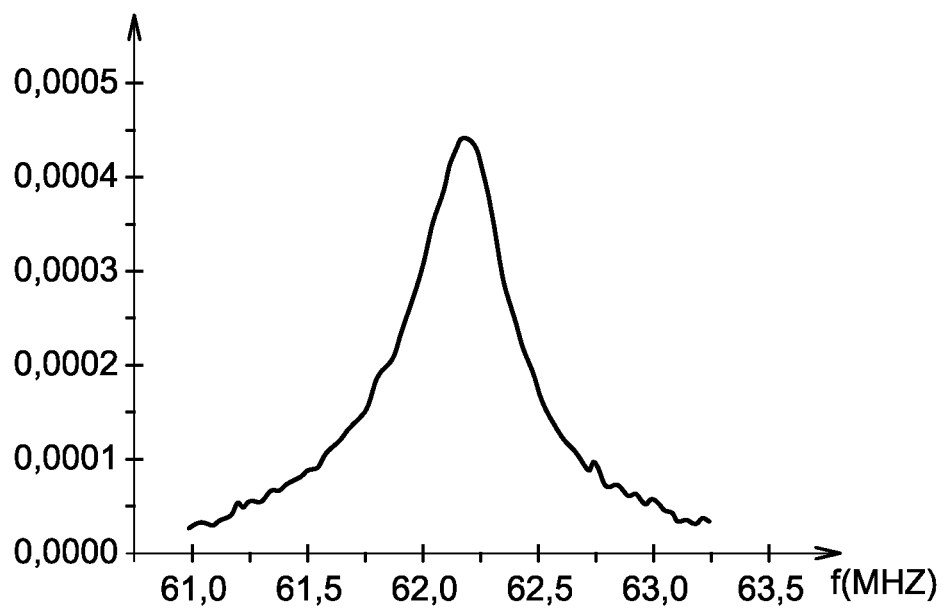
FIGS. 12 and 13 are graphs representing resonance curves for a clamped-free beam of the type represented in FIG. 4, FIGS. 14A and 14B are top views showing the production of a piezoresistive sensor for the detection of gas, respectively before and after functionalization, according to the invention.
Figure 13:
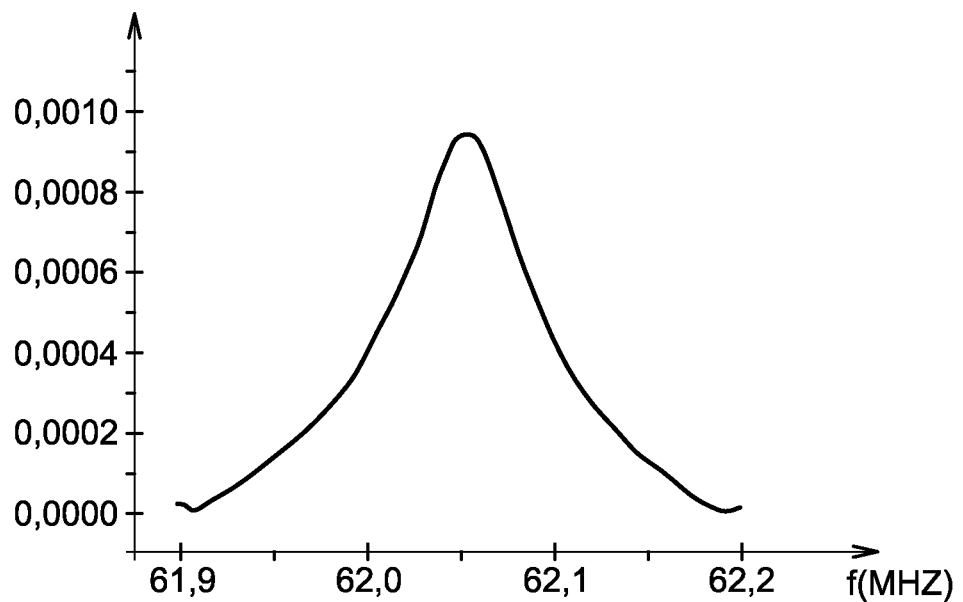

FIG. 12 corresponds to a measurement of the resonance peak in ambient air. FIG. 13 corresponds to a measurement of the resonance peak under a vacuum of $10^{-3}$ torrs. The Y-axis of these graphs corresponds to the voltage in volts of the output signal of the means of detection. The X-axis corresponds to the frequency f of the signal detected. For FIG. 12, the quality factor Q is equal to 200. For FIG. 13, the quality factor Q is equal to 1100. These results are obtained for a RMS alternative voltage of 40 mV.

Other characteristics have been obtained on resonating beams of same shape but with different dimensions (resonance frequency around 5.5 MHz). In all cases, the behaviour obtained is similar to that observed and measured until now on equivalent devices made of SiC or SiN (piezoresistive gauges with 10 nm of gold deposited).

Figure 1:
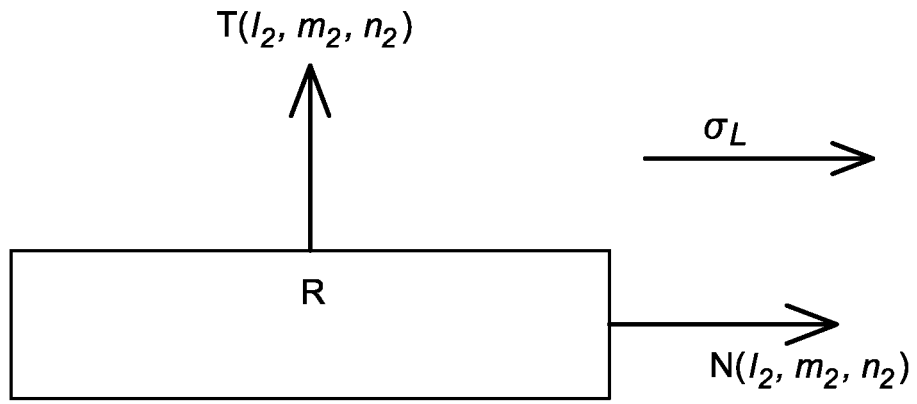
FIG. 1, already described, is a diagram of a piezoresistive gauge and the associated main axes (N, T), FIG. 2, already described, is a diagram illustrating, for several metal materials, the variation in resistance as a function of the deformation of these materials, FIG. 3, already described, is a diagram representing the gauge factor as a function of the resistance of a layer of aluminium.
Figure 2:
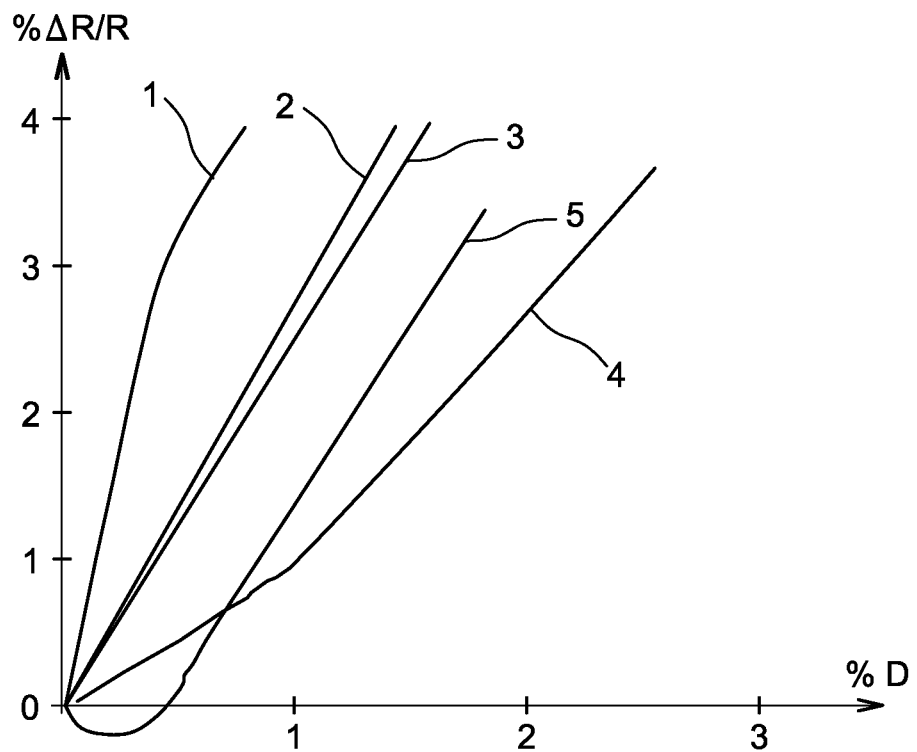
Figure 3:
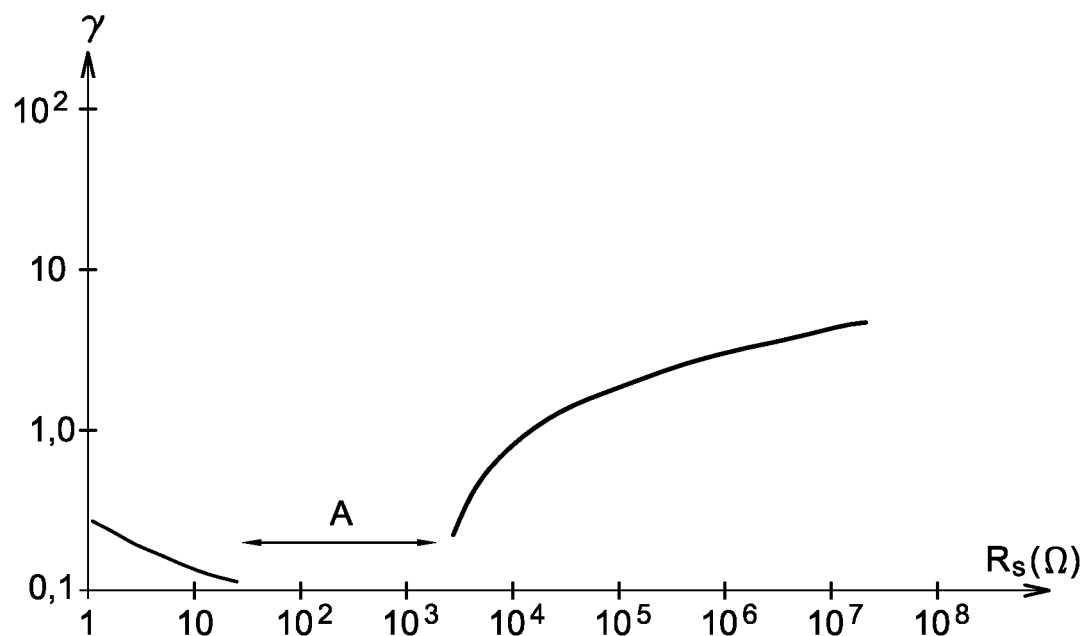

In a surprising manner vis-à-vis the state of the art (see FIG. 3), gauge factors between 2 and 4 (according to the thickness considered) are found experimentally for AlSi for a resistance of 20 Ω, in other words conforming to the known predictions for a metal other than aluminium. The resistivities measured are between 3 and 5 µohms.cm, according to the thickness considered (around 3 µohms.cm for thick films known as "bulk" and close to 4.5 µohms.cm for thicknesses of 60 nm).

For applications of gas detection via the use of functionalization layers, it is shown that the deposition of polymers (based on diazonium) by electro-grafting techniques is carried out preferentially between the silicon and the AlSi on the non-metallised parts.

For example, it is known how to deposit simultaneously 15 to 20 nm of these diazonium salt layers on silicon for only several nanometres maximum on AlSi. Within the scope of a gas detection application (via the adsorption of the molecules to be detected on the functionalization layers), it is thus also possible to use AlSi as current input electrode on the silicon parts (doped or slightly doped) so that the grafting of the functionalization layers only takes place at the chosen silicon spots.

FIGS. 14A to 14C illustrate the formation of a piezoresistive sensor for the detection of gas, according to the present invention.

FIG. 14A shows, in top view, the sensor before its functionalization. It comprises a clamped-free silicon beam 100. The beam 100 is embedded on a support substrate by the anchoring 101. The free end of the beam 100 is covered with a layer of AlSi 102 connected by a current loop 103 to current inputs 104 and 105.

FIG. 14B shows, in top view, the sensor after its functionalization. Its upper surface is covered with a grafting layer spread out in 100' on the silicon beam, in 102' on the layer of AlSi and in 103' on the current loop. The grafting layer also covers in 101' the anchoring of the sensor and in 104' and 105' the current inputs. FIG. 14C is a transversal sectional view along the axis C-C of FIG. 14B. This figure shows the distributions of the grafting layer on the different parts of the sensor.

Figure 15:
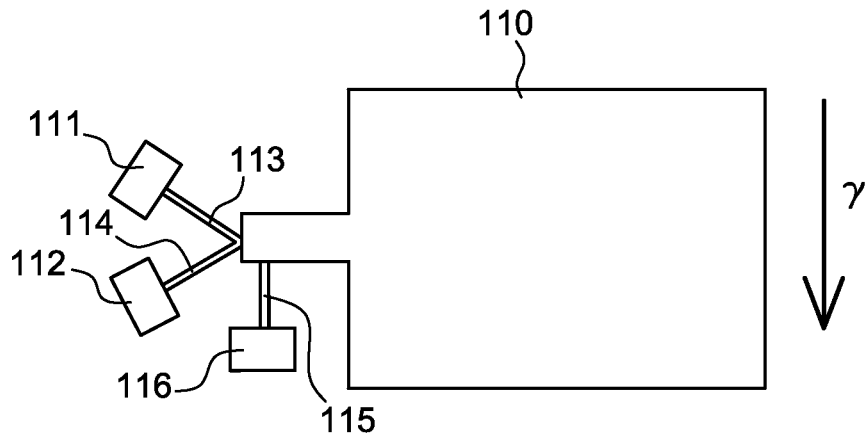
FIG. 15 is a schematic representation of an acceleration sensor using the compression/traction of a strain gauge, according to the invention.

To form an accelerometer, it is possible for example to use the structure illustrated in FIG. 11 as a basis. To these structures must be added a test mass, the movement of which will be a function of an external acceleration. The detection may be through compression/traction of the metallic gauge as shown in FIG. 15. A test mass undergoing an acceleration is going to constrain the gauge placed perpendicularly to the movement created by the acceleration. The reading is then carried out preferentially with a Wheatstone bridge type measuring bridge. The reading can be made in direct current or in alternating current in order to eliminate the noises in 1/f.

FIG. 15 is a schematic representation of an acceleration sensor using the compression/traction of a strain gauge, according to the invention. This figure shows a test mass 110 subjected to an acceleration γ. The test mass is connected to anchoring areas 111 and 112 by suspensions 113 and 114. The reference 115 designates a strain gauge between the test mass 110 and an anchoring area 116. The gauge 115 comprises a layer of AlSi deposited on a nano-silicon beam. The thickness of the AlSi layer may be between 10 nm and 200 nm. The width of the layer is less than, for example, 100 nm. The length to height ratio value of the resonator is for example around 100.

Figure 16:
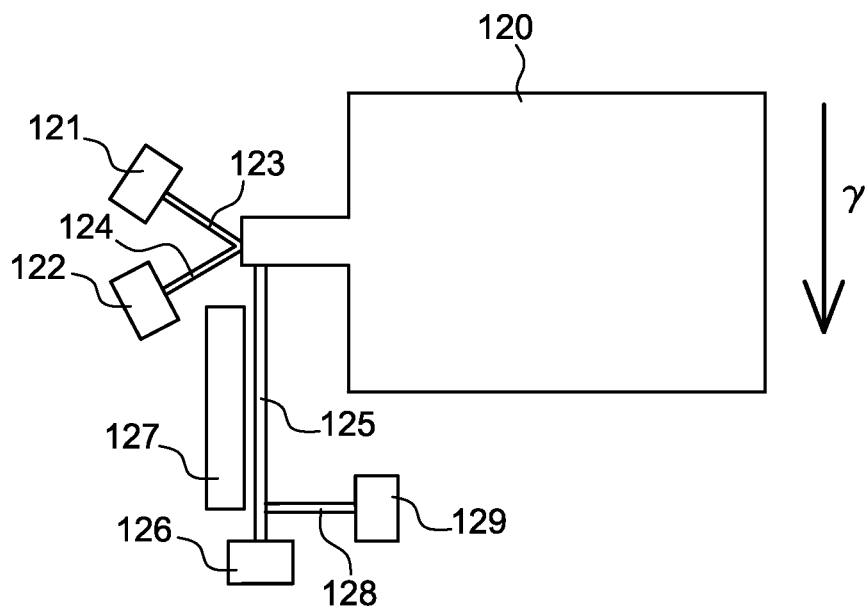
FIG. 16 is a schematic representation of an acceleration sensor with frequency detection using a strain gauge working in traction/compression, according to the invention.
Figure 17:
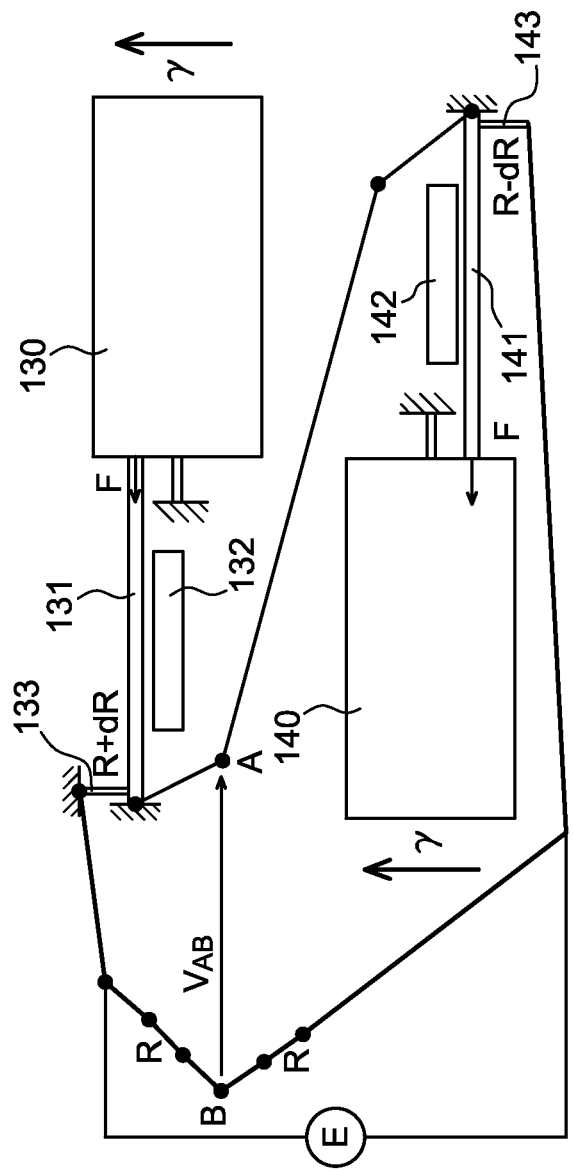
FIG. 17 is a schematic representation illustrating the piezoresistive detection of strain gauges according to the invention and for a Wheatstone bridge measurement.

The gauge can also serve to measure the frequency variation. The movement undergone by the beam is going to induce a strain in a vibrating nano-beam judiciously attached to the test mass. This strain is then going to modulate the resonance frequency. This is measured by AlSi metallised strain gauges and placed perpendicularly to the resonating beam as shown in FIGS. 16 and 17. The AlSi gauge works in traction/compression.

FIG. 16 is a schematic representation of an acceleration sensor with frequency detection using a strain gauge working in traction/compression, according to the invention. This figure shows a test mass 120 subjected to an acceleration γ. The test mass is connected to anchoring areas 121 and 122 by suspensions 123 and 124. The reference 125 designates a resonator arranged between the test mass 120 and an anchoring area 126. Actuating electrodes, designated under the single reference 127, are arranged to activate the resonator 125. A strain gauge 128 is arranged between the resonator 125 and an anchoring area 129 and perpendicularly to the resonator. It works in traction/compression.

The resonator can have a thickness of silicon for example between 100 nm and 2 µm. Its width is greater than or equal to 100 nm. The length to height ratio of the resonator is situated around 100. Its spacing in relation to the actuating electrodes is equal to or greater than 50 nm. Its aspect ratio is equal to or greater than 4. The strain gauge 128 comprises a layer of AlSi, from 10 nm to 200 nm thickness, deposited on a nano-silicon beam. Its width is less than 100 nm. Its length to height ratio is situated around 100, or even less than 100.

The test mass may be formed in the same layer as the gauge. Nevertheless, advantageously this mass is defined in another thicker layer so as to obtain a sufficient inertia.

The reading can be taken according to the diagram of FIG. 17, which is a representation illustrating the piezoresistive detection of strain gauges according to the invention and for a Wheatstone bridge measurement. This diagram shows two test masses 130 and 140 attached to anchoring areas and subjected to an acceleration γ.

A resonator 131 is arranged between the test mass 130 and an anchoring area. This resonator is subjected to a force F generated by the test mass 130 under the effect of the acceleration. Activation electrodes, designated under the single reference 132, are arranged parallel to the resonator 131. Situated perpendicular to the resonator is arranged a strain gauge 133 connected by one end to the resonator 131 and by another end to an anchoring area.

A resonator 141 is arranged between the test mass 140 and an anchoring area. This resonator is subjected to the force F generated by the test mass 140 under the effect of the acceleration. Activation electrodes, designated under the single reference 142, are arranged parallel to the resonator 141. Situated perpendicularly to the resonator is arranged a strain gauge 143 connected by one end to the resonator 141 and by another end to an anchoring area.

The Wheatstone bridge is completed by two fixed resistances R arranged in series in a first branch of the bridge, the strain gauges 133 and 143 being connected in series in the second branch of the bridge. The bridge is supplied under a voltage E.

When the test masses 130 and 140 are subjected to the acceleration γ, a force F is generated in the resonators 131 and 141, which results in variations in resistivity in the gauges 133 and 143, respectively R+dR and R−dR. A voltage variation $V_{AB}$ is measured between the points A and B.

Figure 18:
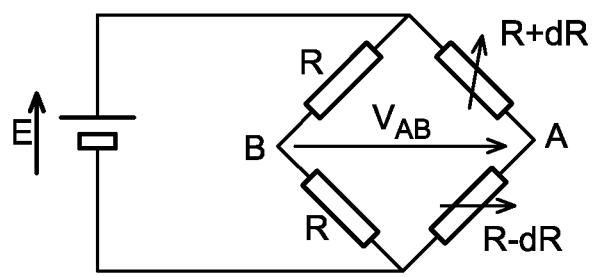
FIG. 18 represents the electrical diagram of the Wheatstone bridge implemented in FIG. 17.

FIG. 18 represents the electrical diagram of the Wheatstone bridge implemented in FIG. 17.

A particularly interesting application of AlSi relates to the very large scale integration (VLSI) of NEMS. Reference may be made in this respect to the following articles:

"Ultimate limits to inertial mass sensing based upon nanoelectromechanical systems" of K. L. Ekinci et al., Journal of Applied Physics, vol. 95, n° 5, 2004, pages 2682 to 2689;

the article of Mo Li et al., cited above,

"A self-sustaining ultrahigh-frequency nanoelectromechanical oscillator" of X. L. Feng et al., Nature Nanotechnology, vol. 3, n° 6, pages 342 to 346.

In the field of inertial sensors, the article "Micromachined inertial sensors" of N. Yazdi et al., Proceedings of the IEEE, vol. 86, n° 8, August 1998, pages 1640 to 1659, may be cited.

The invention claimed is:

1. A nano electro-mechanical system (NEMS), comprising:
    a fixed part associated with a substrate;
    a moveable part, moveable in relation to the substrate; and
    a transduction component comprising an electrically conductive material, which comprises an AlSi alloy based deposition,
    wherein the transduction component is configured to excite the movable part to move the moveable part, to detect a movement of the movable part, or both, and
    wherein the AlSi alloy based deposition is supported at least in part by the movable part and forms two overlapping current loops, one configured to excite the movable part and the other configured to detect movement of the movable part.

2. The system of claim 1, wherein the AlSi alloy based deposition is AlSi or AlCuSi.

3. The system of claim 1, wherein the transduction component further comprises, under the electrically conductive material, an additional layer, and the additional layer is capable of structuring the electrically conductive material, amplifying the movement of the moveable part, forming a barrier to diffusion of the conductive material, or a combination thereof.

4. The system of claim 1, wherein the movable part comprises a clamped-free beam or a clamped-clamped beam.

5. The system of claim 1,
    wherein the substrate comprises a support,
    an electrically insulating layer covers the support,
    a superficial silicon layer covers the electrically insulating layer,
    the superficial silicon layer comprises the fixed part and the movable part, and
    the movable part of the superficial silicon layer covering the electrically insulating layer is moveable because of a hollowing out in the electrically insulating layer.

6. The system of claim 1, further comprising:
    a test mass,
    wherein on end of the movable part is attached to the substrate and another end of the moveable part is attached to the test mass, and
    the transduction component is capable of detecting a movement of the moveable part.

7. The system of claim 1, further comprising:
    a test mass,
    a resonator connecting the test mass to the substrate,
    wherein one end of the movable part is attached to the substrate and another end of the movable part is attached to the resonator, and
    the transduction component is capable of detecting an acceleration.

8. The system of claim 1, wherein the AlSi alloy based deposition has a thickness between 10 and 100 nm.

9. The system of claim 8, wherein the AlSi alloy based deposition has a thickness between 40 and 80 nm.

10. The system of claim 1, further comprising a deposition of an electrografted functionalization layer, in addition to the AlSi alloy based deposition.

11. The system of claim 1, wherein the fixed part, the movable part, and the transduction component constitute a mass sensor, a gas sensor, a biochemical sensor, a force sensor, an inertial sensor, or a pressure sensor, or a combination thereof.

12. The system of claim 1, wherein, in an AlSi alloy of the AlSi alloy based deposition, a silicon content of the AlSi alloy is from 0.5% to 4% in weight.

13. The system of claim 1, wherein, the silicon content of the AlSi alloy is 1% by weight.

* * * * *

UNITED STATES PATENT AND TRADEMARK OFFICE
CERTIFICATE OF CORRECTION

PATENT NO.         : 9,016,125 B2
APPLICATION NO.    : 13/384474
DATED              : April 28, 2015
INVENTOR(S)        : Philippe Andreucci et al.

Page 1 of 1

It is certified that error appears in the above-identified patent and that said Letters Patent is hereby corrected as shown below:

On the title page, Item (54), and in the Specification, Column 1, the Title's information is incorrect. Item (54) and Column 1 should read:

-- NEMS COMPRISING ALSi ALLOY BASED TRANSDUCER --

On the title page, Item (73), the Assignee's name is incorrect. Item (73) should read:

-- (73) Assignees: Commissariat à l'énergie atomique et aux énergies alternatives, Paris (FR); California Institute of Technology, Pasadena, CA (US) --

On the title page, Item (60), the Related U.S. Application Data is incorrect. Item (60) should read:

-- Related U.S. Application Data

(60) Provisional application No. 61/226,419, filed on Sep. 17, 2009. --

Signed and Sealed this
Twenty-fifth Day of August, 2015

Michelle K. Lee
*Director of the United States Patent and Trademark Office*